United States Patent
Null

(10) Patent No.: US 9,833,364 B2
(45) Date of Patent: Dec. 5, 2017

(54) CAST AND IV MEDICAL SHOWER SYSTEM

(76) Inventor: Warren J. Null, Southbury, CT (US)

(*) Notice: Subject to any disclaimer, the term of this patent is extended or adjusted under 35 U.S.C. 154(b) by 58 days.

(21) Appl. No.: 12/616,434

(22) Filed: Nov. 11, 2009

(65) Prior Publication Data

US 2011/0112450 A1  May 12, 2011

(51) Int. Cl.
*A61B 19/00* (2006.01)
*A61F 13/04* (2006.01)

(52) U.S. Cl.
CPC .................................. *A61F 13/041* (2013.01)

(58) Field of Classification Search
USPC ............... 128/849, 856, 877–879, 845–846, 128/881–882; 602/3–6, 20–27; 604/174, 604/179–180; 2/16, 59, 61, 239, 242, 2/243.1
See application file for complete search history.

(56) References Cited

U.S. PATENT DOCUMENTS

| | | | | |
|---|---|---|---|---|
| 4,327,448 A * | 5/1982 | Lunt | | 2/404 |
| 4,911,151 A * | 3/1990 | Rankin | | A61F 15/004 128/849 |
| 4,986,265 A * | 1/1991 | Caponi | | A61F 13/041 128/846 |
| 5,592,953 A * | 1/1997 | Delao | | A61F 15/004 128/882 |
| 6,267,115 B1 * | 7/2001 | Marshel | | 128/877 |
| 6,276,364 B1 * | 8/2001 | Warner | | A61F 15/004 128/846 |
| 6,512,158 B1 * | 1/2003 | Dobos | | A61F 15/004 602/3 |
| 6,916,301 B1 * | 7/2005 | Clare | | 602/3 |
| 7,290,290 B2 * | 11/2007 | Treadway Fancher | | A61F 13/06 2/16 |
| 8,206,363 B2 * | 6/2012 | Bainbridge | | A61B 46/27 604/293 |
| 2004/0215118 A1 * | 10/2004 | Dumas | | A61F 15/004 602/3 |
| 2006/0253055 A1 * | 11/2006 | Lindbery | | 602/3 |
| 2007/0083163 A1 * | 4/2007 | Rydell | | 604/174 |
| 2008/0108964 A1 * | 5/2008 | Edwall | | 604/385.3 |

* cited by examiner

Primary Examiner — Nina Bhat

(57) ABSTRACT

A disposable Cast and Intravenous (IV) Medical Shower System for protecting casted and/or IV therapy injected appendages from moisture while a patient is showering or bathing. A plurality of embodiments are disclosed, including a variety of sizes and colors for a variety of users for a variety of applications to accommodate a variety of limbs and afflictions such as wounds with or without a bandages, IV or drain lines, and fixed casts. One embodiment of the system is characterized by flexible stretch vinyl in a tubular shape with only one opening, which creates a water tight seal between the appendage and the system. Additionally, the midsection torso embodiment has an optional pocket on the inside surface (facing the skin) that is used for housing a medical device such as an insulin pump or pocket health monitor. Finally, the process for making and using the system is described in full detail.

6 Claims, 12 Drawing Sheets

ARM TO ELBOW

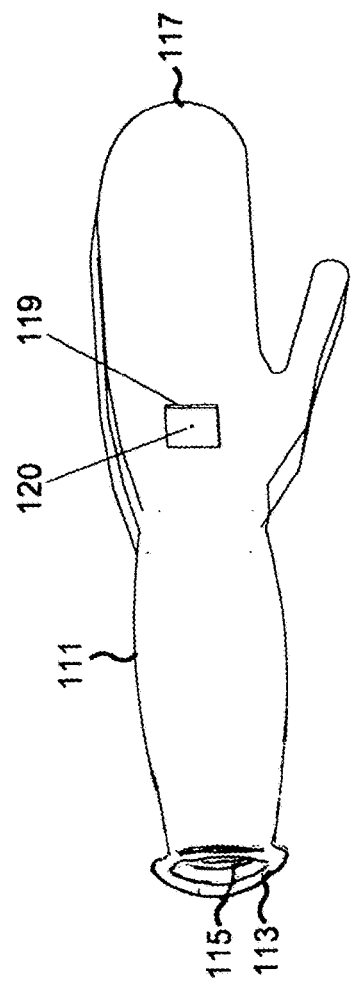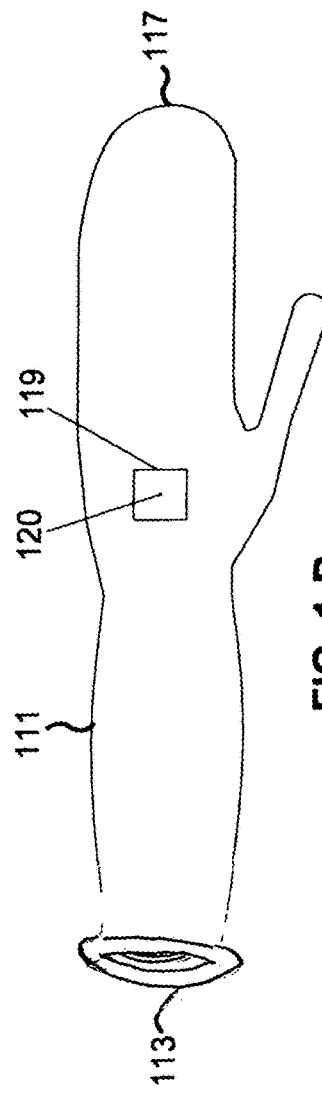

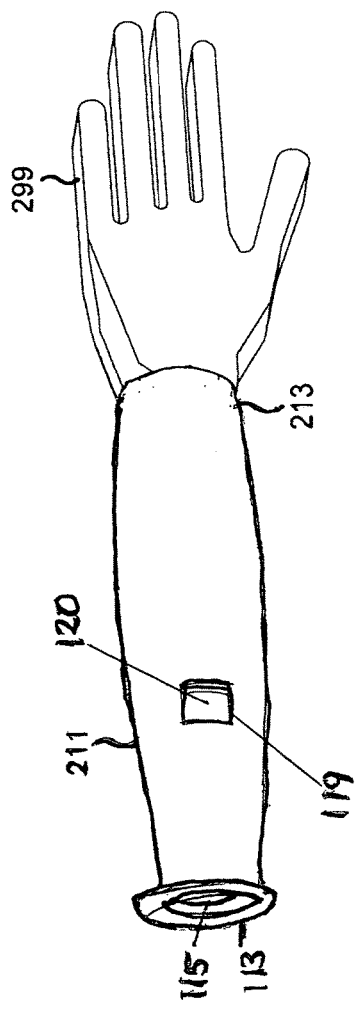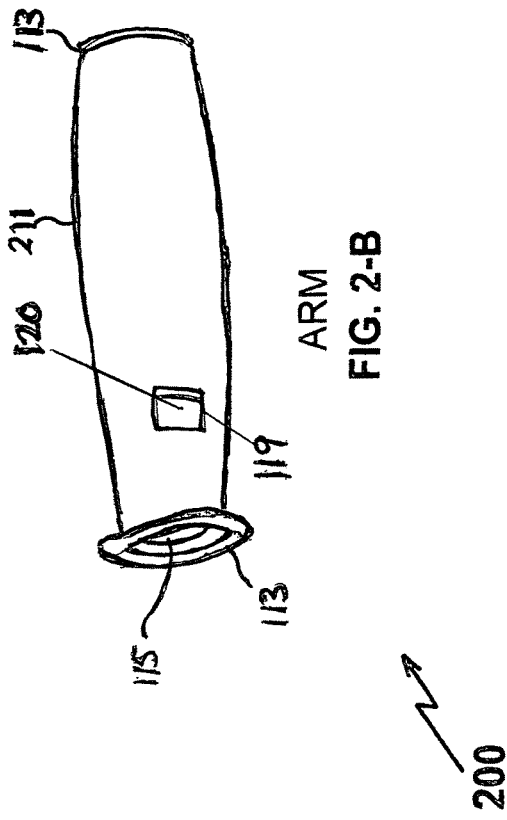
ARM TO ELBOW
FIG. 2-A
ARM
FIG. 2-B

NECK

MID SECTION

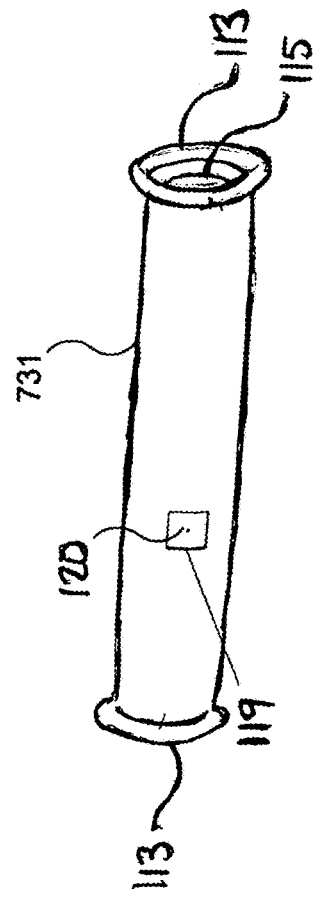
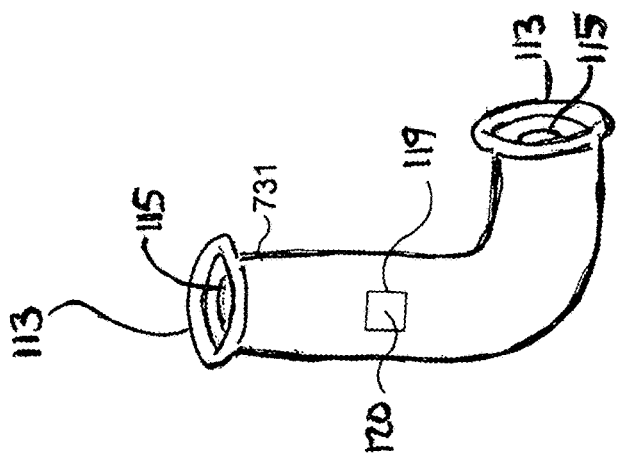
ARM & ELBOW
FIG. 7-B
ARM & ELBOW
FIG. 7-A

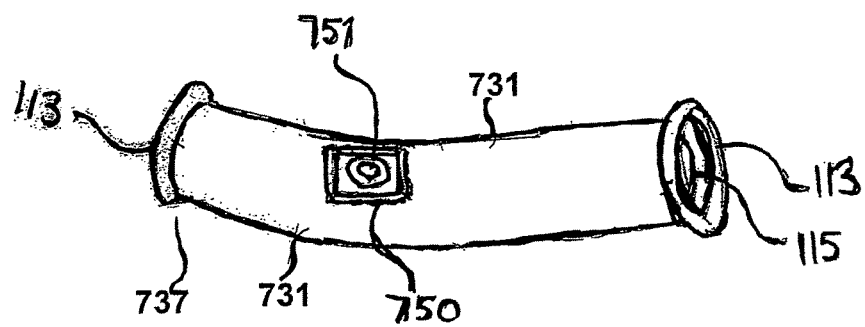
IV & PICC COVER
FIG. 7-C
700

POCKET TO HOLD INSULIN PUMP OR MEDICAL MONITOR

CAST AND IV MEDICAL SHOWER SYSTEM

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable

STATEMENT REGARDING PRIOR DISCLOSURES BY THE INVENTOR OR A JOINT INVENTOR

Not Applicable

BACKGROUND OF THE INVENTION

(1) Field of the Invention

This disposable cast and IV medical shower system of this invention relates to methods, devices, and system for protecting a patient with a cast or wound with or without a bandage, or an Intravenous (IV) therapy line or drain line attached to an appendage from getting the cast, bandage, wound, drain line or IV site wet during a shower, bath, or swimming.

This invention eliminates the need for this securing mechanism, thereby reducing production cost, shipping cost, and cost to the customer.

More specifically this device allows the patient to independently maintain personal hygiene without the need of a nurse or assistant, and without the worry of damaging the medical implements or creating infection due to the water from the shower.

The problem with prior art cast covers designed for bathing and showering is that they tend to be expensive to manufacture and package, and include a hard, bulky circular mechanism for securing the device onto the protected appendage. While this hard circular mechanism is necessary to secure the device, it reduces patient flexibility as well as increases production and shipping costs. Furthermore, prior art devices are not disposable.

(2) Description of Related Art Including Information Disclosed Under 37 CFR 1.97 and 1.98

A prior art search was not commissioned because the inventor is intimately familiar with the prior art. A prior art patentability search was neither commissioned nor conducted by the inventor, but the inventor is intimately familiar with the prior art. Many inventors have designed protection devices to keep cast, bandages, and IV connections dry and hygienic during patient showers. None of the prior devices, however, include the flexibility, simplicity, durability, affordability and disposability of the current invention. Additionally, unlike prior devices, the current invention includes a reliable water seal. The solution provided by the present inventor is elegantly simple, cost effective, and intuitive. Prior art devices include ordinary plastic bags secured to the appendage in various ways, inflatable cast covers made of latex or similar material, and waterproof cast covers with hard, bulky securing mechanisms. The following are typical examples of the prior art known to the applicant and/or his attorney arranged in reverse chronological order, starting with the most recent for ready reference to the reader.

a). United States Non-Provisional Utility U.S. Pat. No. 6,267,115 B1 bestowed upon Florine Marshel of Foxridge, Md. on Jul. 31, 2002 for, "Intravenous Protecting Device"
b). United States Non-Provisional Utility U.S. Pat. No. 4,986,265 awarded to Ronald E. Caponi of Orlando, Fla. on Jan. 22, 1991 for, "Protective Cover for Cast"
c). United States Non-Provisional Utility U.S. Pat. No. 4,966,135 bestowed upon Bruce Renfrew of San Mateo, Calif. on Oct. 30, 1990 for, "Orthopedic Cast Cover and Method of Manufacture.
d). United States Non-Provisional Utility U.S. Pat. No. 4,363,317 earned by Daniel Broucek of Grand Rapids, Mich. on Dec. 14, 1982 for, "Watertight Cast Cover"
e) U.S. Pat. No. 4,043,326 granted to Little et al on Aug. 23, 1977 for "Waterproof Cast Protector"

BRIEF SUMMARY OF THE INVENTION

The cast and IV medical shower system is a watertight system designed to protect patients with casts, wounds (with or without bandages), and/or intravenous (IV) therapy sites or drain lines on their hands, arms, feet, legs, or other limb, body part or appendage from getting the limb or body part wet during a shower, bath or swimming. The proposed solution is a Cast and Intravenous (IV) Medical Shower System that protects casted and/or IV therapy injected appendages from moisture while a patient is showering. Pluralities of embodiments are disclosed. One embodiment of the system is characterized by flexible stretch vinyl in a tubal shape with only one opening, which creates a water tight seal between the appendages and the system. The mid-section torso embodiment also has an optional pocket on the inside surface facing the skin for housing a medical device such as an insulin pump or pocket health monitor. The invention reduces the risk of infection to the appendage or damage to a protected cast or bandage by eliminating the chance of water infiltration.

OBJECTIVES OF THIS INVENTION

1. To provide methods, devices, and a system for protecting an appendage from getting wet during a bath or shower.
2. To provide protection of an appendage encased in a cast during a bath or shower.
3. To provide waterproof protection of a bandaged appendage during a bath or shower.
4. To hygienically protect an intravenous (IV) therapy site on an appendage by shielding said site from water during a bath or shower
5. To protect an appendage from the elements during inclement weather conditions.

6. To be applied, secured, and removed with ease by a user that has functional use of only one hand or arm.

7. To be an economical alternative to prior art solutions.

8. To be easy to use, even intuitive, and require little additional training for patient or hospital staff.

9. To allow a casted, bandaged, and/or IV receiving patient to independently maintain personal hygiene without the additional expense of a nurse or medical assistant.

10. To allow a casted, bandaged, or IV receiving patient to take a shower without the fear of risking infection or damaging medical equipment.

11. To be physically safe in a household or medical environment.

12. To be easy to transport and store.

13. To meet all federal, state, and local standards and guidelines with respect to safety, environment, and quality.

14. To be designed with ease of use, simplicity and elegance.

15. To provide plurality of flexible modes of operation.

16. To be capable of multiple uses.

17. To be simple to use and require no additional training.

18. To provide an integrated solution.

19. To meet or exceed most of the applicable federal, state, local and other private standards, guidelines, regulations and recommendations with respect to safety, environment, and energy consumption.

20. To permit disposal after single use.

21. To provide a variety of sizes to fit either children or adults as well as provide colorful aesthetics designed to please, appease, and even entice children to take a bath under trying circumstances.

22. To be made from modular standard materials, and components that are also easily maintainable.

23. To be highly reliable and carry high MTBF (High Mean Time between Failures) due to fire resistant tubing and components.

24. To reduce the insurance premiums for liability insurance of the medical service or healthcare provider 25. To prevent any harm to patients, their visitors, and any staff attending the patients.

Other objectives of this invention reside in its simplicity, elegance of design, ease of manufacture, service and use, and even aesthetics. These will become apparent from the following brief description of the drawings as well as a detailed description of the concept embodiment.

BRIEF DESCRIPTION OF THE DRAWINGS

FIG. 1A is an isometric view of the wrist and hand full cover embodiment of the subject invention shown with the optional IV window.

FIG. 1B is a perspective view of the wrist and hand full cover embodiment of the subject invention with the optional IV window FIG. 2A is an isometric view of the arm to elbow partial cover embodiment of the subject invention with the user's hand shown extending through the opening. The optional IV window is shown in this embodiment.

FIG. 2B is an isometric view of the arm to elbow partial cover embodiment of the subject invention not in use. The optional IV window is shown in this embodiment.

FIG. 7A-7B shows the arm and elbow cover of the invention.

FIG. 7C shows the IV and PICC cover of the invention.

DETAILED DESCRIPTION OF THE INVENTION

Figure 3:
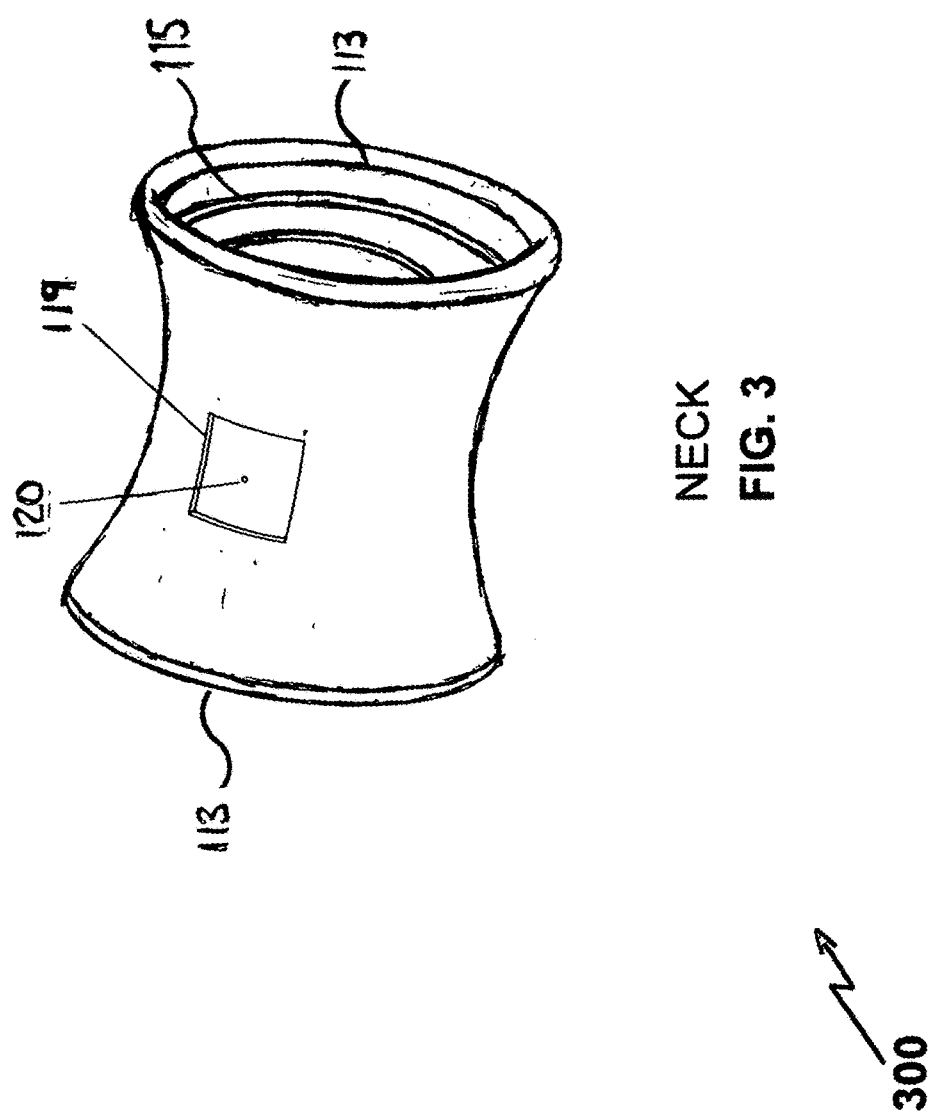
FIG. 3 is an isometric view of the neck protecting embodiment of the subject invention.

In this detailed description of the preferred and alternate embodiments, pluralities of embodiments are disclosed. As shown in the drawings, wherein like numerals represent like parts of various figures, FIG. 1A is an isometric view of the wrist and hand full cover embodiment of the subject invention shown complete with the IV optional window 119 with hole 120, hand mitten 111 having open end 115 including a molded ring_13 and closed end 117. Likewise, FIG. 1B is a perspective view of the wrist and hand full cover embodiment of the subject invention complete with the optional IV window 119 with hole 120, hand mitten 111 having open end 115 including a molded ring 113 and closed end 117. The disposable full cover embodiment of the invention for protecting an arm (upper appendage) that is casted or bandaged in any region from the fingers to wrists is shown as 100 in FIG. 1A and FIG. 1B. As illustrated in FIG. 1A and FIG. 1B, the molded ring 113 is molded to the vinyl protective sleeve 111 to create the opening hole 115 of the invention. Said opening hole 115 has a diameter that is less than the diameter of the appendage to be protected. In this embodiment designed for protecting the upper appendage, the user's hand is inserted through said opening hole 115. The invention is then slid over the cast/bandaged arm portion extending the protective sleeve 111. Said opening hole 115 stretches to accommodate the size and shape of the user's arm while creating a water tight seal. The length of the protective sleeve 111 can vary. The embodiment of the invention shown in FIG. 1A and FIG. 1B can be longer to provide protection from the user's fingers to the elbow. The system is designed so that it can be easily applied by patients with full use of only one arm (upper appendage). FIG. 2A is an isometric view of the arm to elbow partial cover embodiment of the subject invention with the user's hand 299 shown extending through the opening. The optional IV window 219 with hole 220 in the glove 211 having a pair of open ends 215 and molded ring 213 at each end. Glove 211 is designed to snugly yet comfortably fit fingers 299. Similarly, FIG. 2B is an isometric view of the arm to elbow partial cover embodiment of the subject invention not in use. The optional IV window 219 with hole 220 in the glove 211 having a pair of open ends 215 and molded ring 213 at each end. The partial cover embodiment of the invention for protecting a casted or bandaged region on the upper appendage is shown as 200 in FIG. 2A and FIG. 2B. As illustrated in FIG. 2A, the patients hand 221 is inserted in one opening hole 215 and exuded through the opening hole 215 on the opposite end. The partial cover embodiment shown in FIG.

2A and FIG. 2B can be extended to protect the upper appendage from the wrist to the shoulder.

Figure 4:
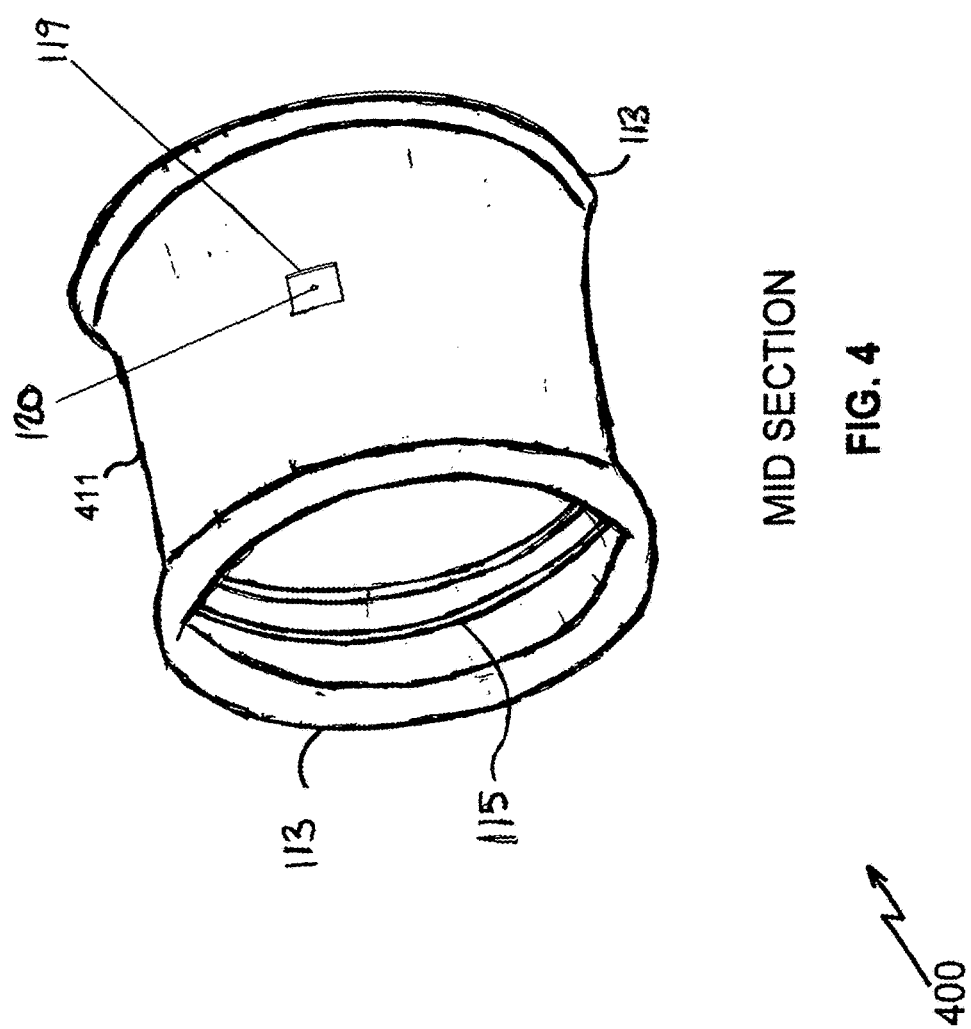
FIG. 4 is an isometric view of the midsection protecting embodiment of the subject invention. The optional IV window is shown in this embodiment.
Figure 5:
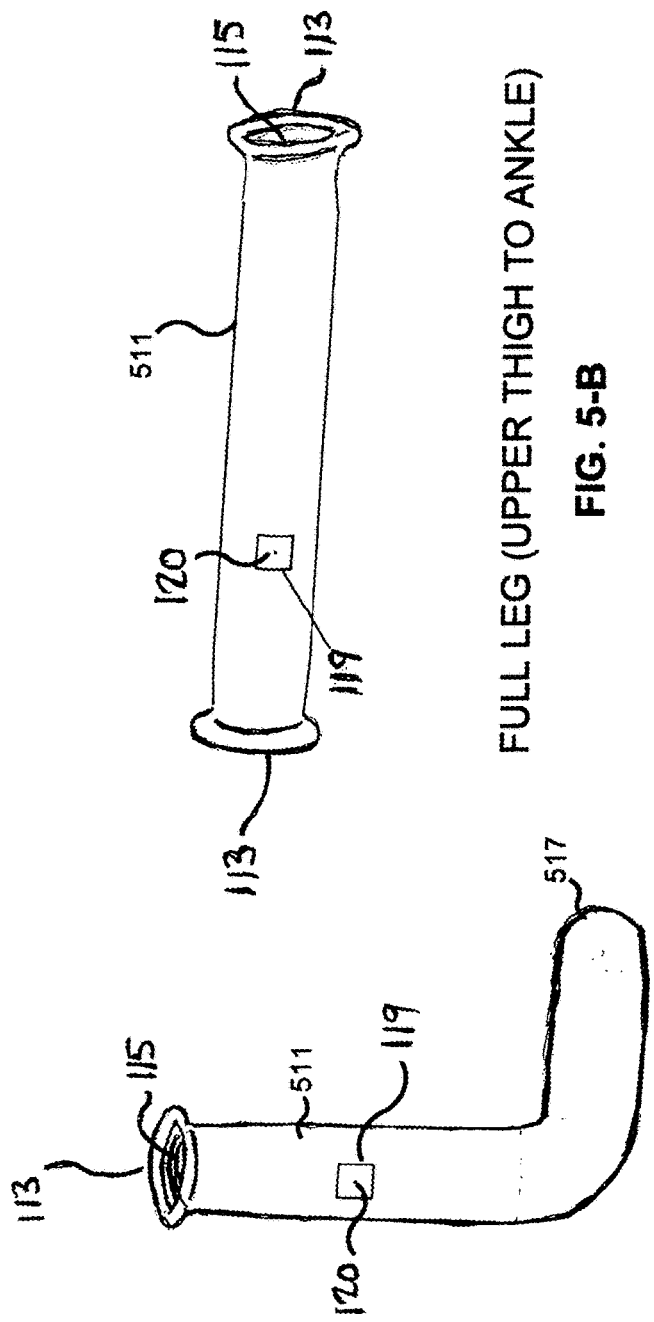
FIG. 5A is an isometric view of the foot and leg full cover embodiment of the subject invention.
FIG. 5B is an isometric view of the upper thigh to ankle partial embodiment.
Figure 6:
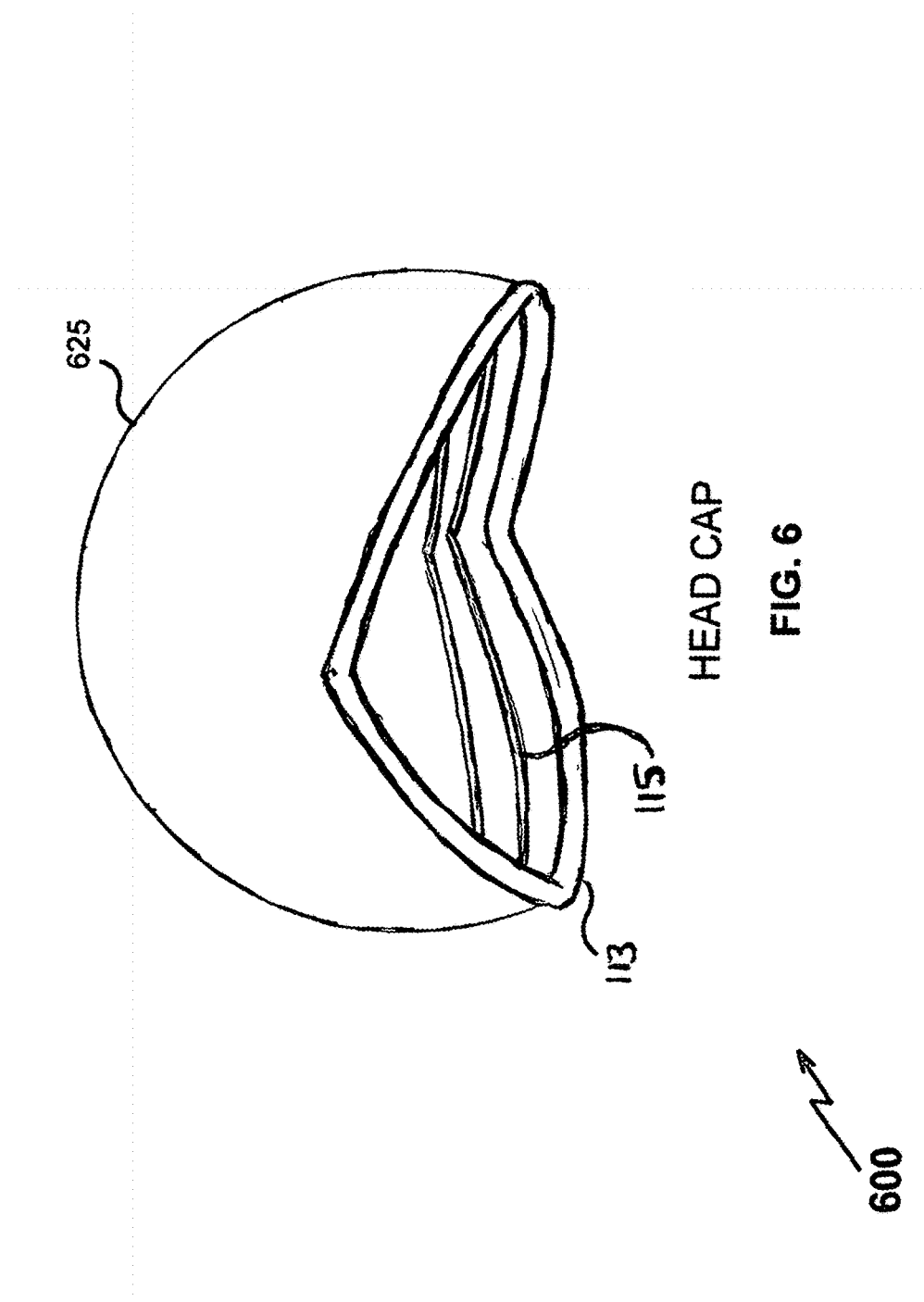
FIG. 6 is an isometric view of the head cap embodiment of this invention.
Figure 8:
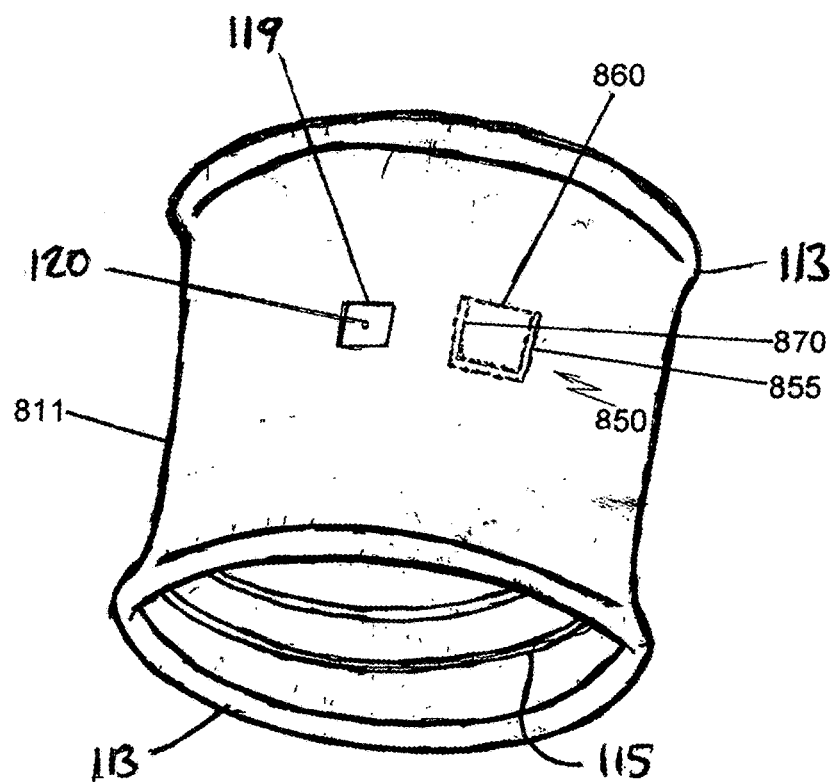
FIG. 8 shows the pocket to hold and insulin pump or medical monitor cover of the invention.
Figure 9:
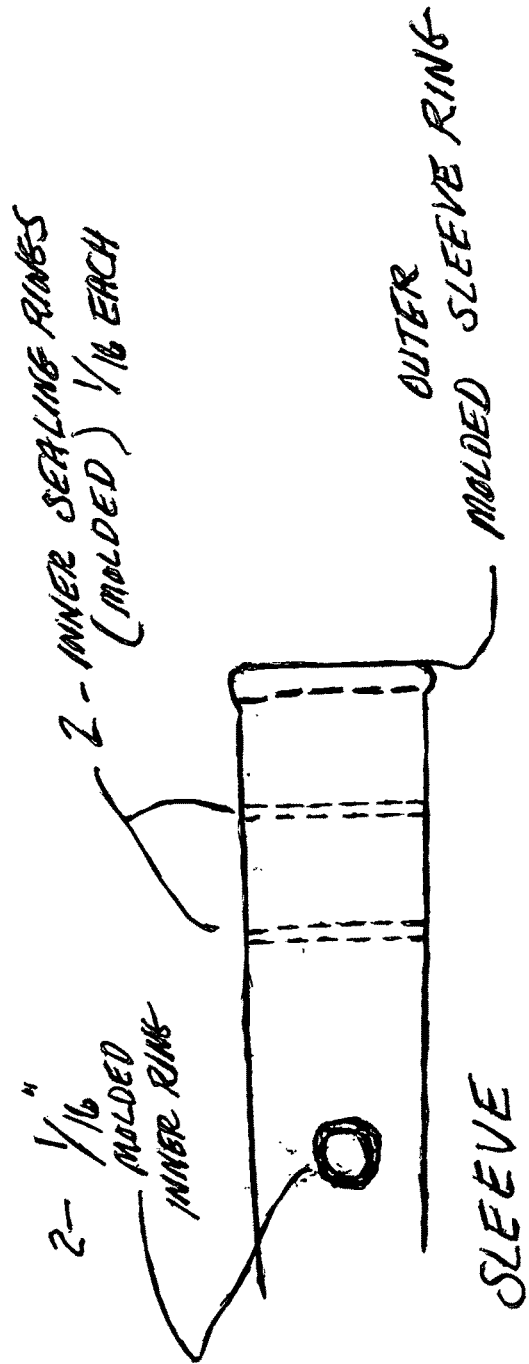
FIG. 9 shows the triple seal protection of the cover.
Figure 10:
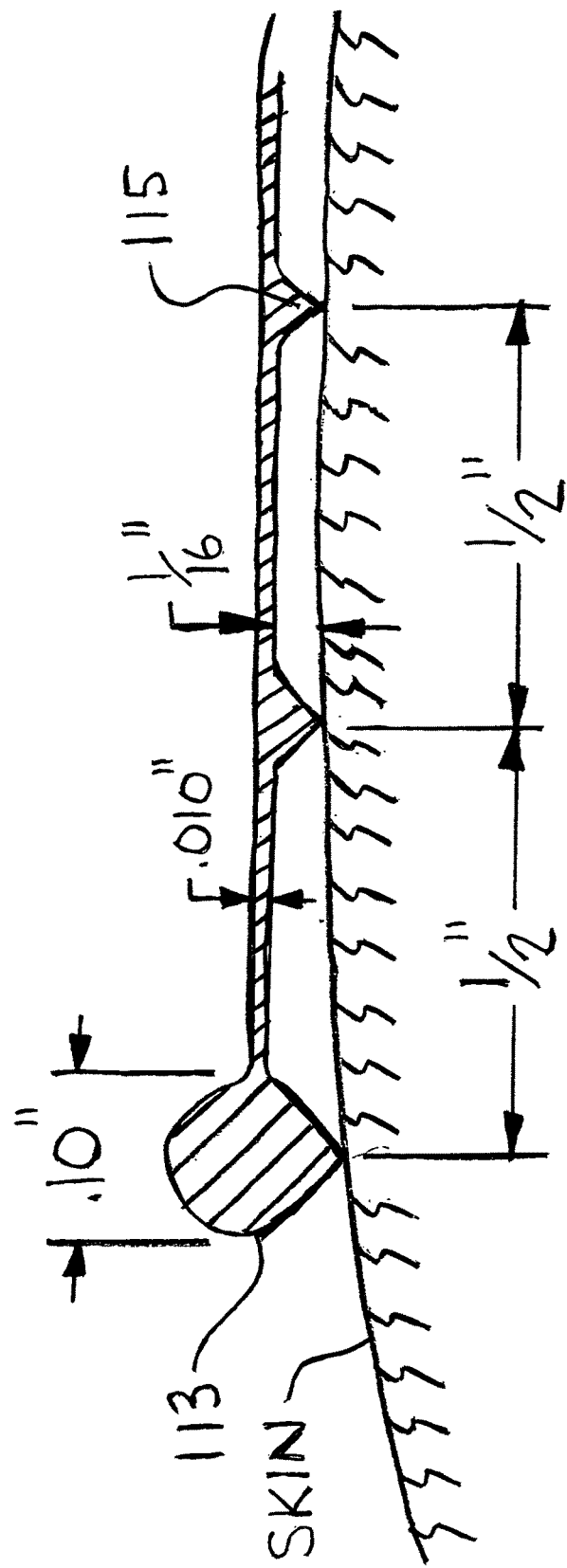
FIG. 10 shows the covering over the skin.
Figure 11:
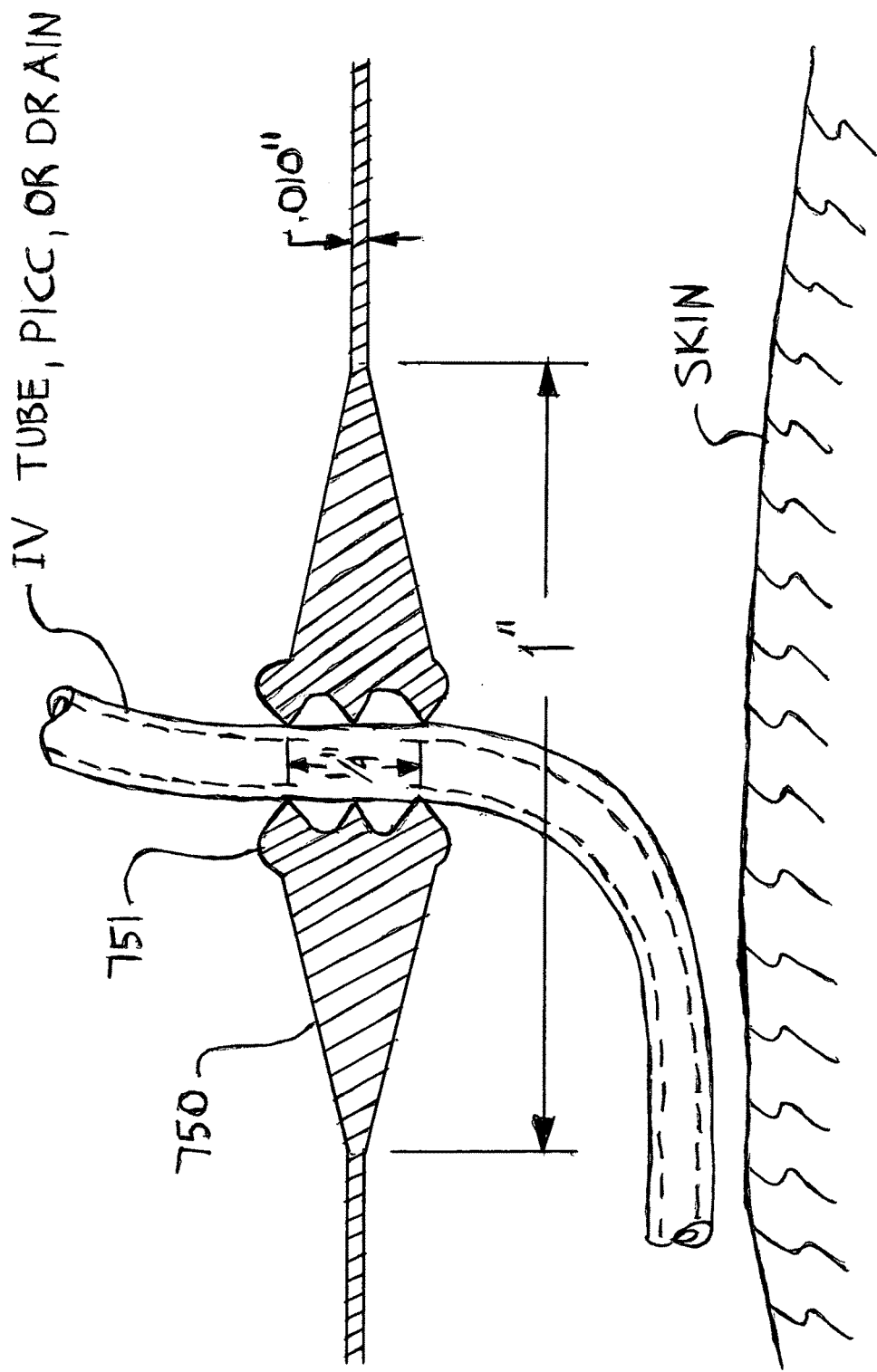
FIG. 11 shows the cover in relation to the IV, Tube, PICC or Drain.

FIG. 3 is an isometric view of the neck protecting embodiment shown complete with molded ring 313 near opening hole 315, optional intravenous therapy window 319, and concomitant hole 320 for the IV line. The neck protecting embodiment of this invention is shown as 300 in FIG. 3. The molded ring 313 is molded to each end of the protective sleeve 311 to create two openings that each have a diameter less than the diameter of the user's neck. The patient uses this embodiment by sliding both of the opening holes 315 over their head and onto their neck. The diameter of the opening hole 315 expands to allow the patient to slide the invention over their head and create a watertight seal around the patient's neck. This embodiment protects the bandaged portion of the patient's neck from shower water while in use. FIG. 4 is an isometric view of the midsection protecting embodiment of the subject invention complete with stretch vinyl protective sleeve 411, V-ring 413, and ingress and egress opening hole 415. The optional IV window is also shown in this embodiment. The midsection protecting embodiment of this invention is shown as 400 in FIG. 4. The molded V-ring 413 is molded 'to each end of the protective sleeve 411 to create two openings that each has a diameter less than the diameter of the user's torso. This midsection torso embodiment also includes an optional pocket (not shown) on the inside surface facing the skin for housing a medical device such as an insulin pump or pocket health monitor. The invention is applied by the patient by placing both feet through both of the opening holes 415. The entire invention is slid above the patient's waist and secured around the patient's midsection. Said opening holes expand to create a watertight seal around the patient's midsection. FIG. 5A is an isometric view of the foot and leg cover embodiment of the subject invention complete with foot and leg stretch vinyl protective sleeve 511, molded V-ring 513, ingress egress opening hole 515 and closed end 517 for the toes. Also shown is IV therapy window 519 with concomitant hole 520 for the intravenous line if the case admits one. The midsection protecting embodiment of this invention is shown as 400 in FIG. 4. The molded V-ring 413 is molded 'to each end of the protective sleeve 411 to create two openings that each has a diameter less than the diameter of the user's torso. This midsection torso embodiment also includes an optional pocket (not shown) on the inside surface facing the skin for housing a medical device such as an insulin pump or pocket health monitor. The invention is applied by the patient by placing both feet through both of the opening holes 415. The entire invention is slid above the patient's waist and secured around the patient's midsection. Said opening holes expand to create a watertight seal around the patient's midsection. FIG. 5A is an isometric view of the foot and leg cover embodiment of the subject invention complete with foot and leg stretch vinyl protective sleeve 511, molded V-ring 513, ingress egress opening hole 515 and closed end 517 for the toes. Also shown is IV therapy window 519 with concomitant hole 520 for the intravenous line if the case admits one. Likewise, FIG. 5B is an isometric view of the upper thigh to ankle partial embodiment complete with sleeve 511 with a pair of open ends 515 each with ring 513, and IV therapy window 519 with concomitant hole 520 for the intravenous line if the case admits one. The full cover embodiment of the invention designed for leg (lower appendage) protection is shown in FIG. 5A, and operates similar to the embodiment designed for arm protection. The foot of the patient is inserted into the system with the opening hole 515 taking the size and shape of the leg (lower appendage). The closed end 517 is shaped like a sock and covers the patient's foot when in use. The partial cover embodiment of the invention designed for leg protection is illustrated in FIG. 5B. This embodiment can be used to protect any portion of the patient's leg from the ankle to the upper thigh. The opening hole 515 has a diameter that is less than the diameter of the patient's leg when the invention is not in use. The patient uses this embodiment by putting their foot through both of the opening holes 515. The lower opening hole remains near the patient's ankle, while the higher opening is adjusted on the patient's leg to cover the water protected region. FIG. 6 is an isometric view of the head cap 625 embodiment of this invention complete with head covering 625 and V-ring 613 on the open end of the head cover 625 for obviating accidental slippage. The embodiment of the invention designed to protect parts of the head and scalp from water is best shown in FIG. 6. The V-ring 613 is molded to the vinyl protective cap 625, creating an opening hole 615 that is smaller than the diameter of the patient's head. The embodiment of the system is also characterized by flexible stretch vinyl in a tubal shape with only one opening which creates a watertight seal between the appendage and the system. Since some of the components of this invention such as head embodiment 600 are amenable to the injection molding process, the inventor is pleased to provide the following description to complete the teaching for a person of average skill in the art. Injection molding is a process that has been in use since the 1920s and provides versatility almost unmatched in the mass production of any material. It requires that melted vinyl be forcefully injected into relatively cool molds. As the vinyl begins to harden, it takes on the shape of the mold cavity and, when cool, requires few post molding operations. Other advantages of this process include its speed of production and the ability to simultaneously manufacture multiple parts. Blow molding in the production of vinyl shapes is a form of extrusion, a major technique in the vinyl industry. Extrusion is used to push a molten tube, called a parison, into a bottle-shaped mold. Compressed air then forces the parison against the cold walls of the mold, hence the term "blow molding." Molds are generally side fed, with the thickness controlled by a tapered mandrel (core) or a variable-orifice die. Continuous extrusion is possible by the use of multiple blow molds. Potential problems that might arise during the development of Safe-N-Sound should be amenable to a resolution through normal product testing and refinement processes, after which we would anticipate the product could be produced routinely. We recommend, however, that an interested company should be allowed to do their own form of testing and marketing and to provide modification suggestions.

ASSEMBLY USE AND OPERATION

The use of this invention is very simple, even intuitive because it comes in a variety of shapes that are approximately the same as the appendage it is designed to protect. An appendage in need of shielding is placed in the opening of the device and the device is then extended along the length of the appendage. Another embodiment of the system is characterized by stretch vinyl in a cylindrical shape with openings on both ends. Embodiments of this invention can also include an IV window opening in the cylinder wall for the extension of the IV insert. All openings of this embodiment are molded with a V-ring to create a watertight seal when in use. The embodiment of the invention used for protecting IV therapy sites on a patient includes the optional IV therapy window (119, 219 . . . etc.) as illustrated in FIG. 1A, FIG. 1B, FIG. 2A, FIG. 2B, FIG. 5A, and FIG. 5B. The IV therapy window will be approximately one and half inches by one and half inches.

The window will be created by building up the area with vinyl to a half inch of thickness. A small hole (120, 220 . . . etc.) is then placed in said to allow access for the IV therapy tubing. The IV therapy window is an optional part of this invention. Typically this invention is a single use disposable type. It can be made in a variety of sizes and colors to suit the needs and aesthetics of everybody, including children, ladies, and the elderly. The IV therapy window (119, 219 . . . etc.) of this invention is used as follows. Before applying the invention to the appendage, the patient's intravenous tube is first disconnected from the supply line and sealed using a heparin lock. The IV insert is left in place and the patient's appendage remains in place. The protective sleeve (111, 211 . . . etc.) is placed over the appendage receiving the IV therapy. The upper most opening hole (115, 215 . . . etc.) is expanded and placed over the IV insert. The end of said IV insert is maneuvered from inside the protective sleeve (111, 211 . . . etc.) to the outside of said protective sleeve (111, 211 . . . etc.) through the hole (120, 220 . . . etc.) in the IV therapy window (119, 219 . . . etc.) The diameter of said hole in the IV therapy window hole (120, 220 . . . etc.) is smaller than the diameter of the IV insert tube, allowing the window to conform to the shape of the tube and creating a waterproof seal. The seal at the opening hole (115, 215 . . . etc.) of the invention is also waterproof, allowing the patient to take a shower without fear of wetting or damaging the connection between the IV insert and the arm. Any cast or bandage on the patient's arm will also be shielded from water when this embodiment is applied over it. The waterproof seal can be readily manufactured with molding technology well known to a person of average skill in the art. The device has a multitude of sizes so that it can fully over appendages on a variety of body types. The term appendages as used herein refer to a forearm and arm (upper appendage), leg and thigh (lower appendage), neck, midsection or torso, and head. The full cover cast protecting embodiment of the hygiene system can also be used to protect bandaged areas that are required to stay dry. This embodiment of the invention has a tubular shape with an opening only on one end. The closed end of the system is either mitten shaped or sock shaped, to fit over the user's hand or foot. The main portion of the system is made of stretch vinyl with a molded shape V-ring molded to the vinyl at said open end. The V-ring portion of the invention creates an opening at said end with a diameter that is much smaller than the diameter of the protected appendage when not in use. When the casted appendage is placed in the system through said end, the aforementioned opening conforms to the size and shape of the appendage, creating a watertight seal. The length and size of the protective sleeve of the invention can vary depending on the appendage protection desired. The medical shower systems for use on the arm can range from finger-to-wrist length to finger-to-shoulder length. Hygiene systems for use on the leg can range from toe-to-ankle length to toe-to-full leg length. A partial cover embodiment of this system can be used for keeping an appendage dry while allowing the user the unhindered use of their extremities. When used on a patient's arm, this embodiment can be of any length to secure dryness from the patient's wrist up to the patient's shoulder. The partial cover embodiment is similar to the full cover embodiment with the exception that there are openings on opposite ends of the system. The additional opening gives the system an open tubular shape. As in the full cover embodiment, the openings of the system are expandable though initially smaller than the diameter of the covered appendage. This allows the partial cover to be placed on an arm in a sleeve like manner while producing a waterproof seal. Moreover, this embodiment can be enlarged appropriately to meet the dimensions of a user's leg or torso. It will additionally range in length so that only the necessary portion of the appendage is covered. When used on the patient's leg, this embodiment can be of any length to secure dryness from the patient's ankle to the patient's upper leg. The IV protecting embodiment of this invention has a design such that a waterproof seal is created over a cast, bandage or IV therapy site, while still allowing the user access to the IV tubing. The IV protecting embodiment has the same shape as either the full cover or partial cover embodiments with an additional opening along the cylindrical wall which serves as an IV window. The IV window will be created by building up the area with vinyl to a half inch of thickness. A small hole is then placed to allow access for the IV tubing sealed by a Heparin Lock (Hep-Lock). The patient's appendage and attached IV tube are inserted through the first opening hole in the protective sleeve. In a partial cover embodiment, the patient's extremities are extended through the second opening hole. The IV tube is extended from within the interior of the protective sleeve to the exterior portion of the sleeve through a small hole in the polyurethane film of the IV window. This hole has a diameter that is less than the diameter of the IV tubing. When said IV tubing is inserted through the IV window, the vinyl expands to accommodate the tubing, creating a watertight seal. The applicant has described the essence of this invention. While the invention has been described with reference to an illustrative embodiment, this description is not intended to be construed in a limiting sense. Various modifications and combinations of the illustrative embodiments as well as other embodiments of the invention will be apparent to a person of average skill in the art upon reference to this description. A skilled artisan will be able to produce the intended invention with the most efficient dimensions of any of the embodiments contained within the description.

VARIATIONS OF THE INVENTION

Due to the simplicity and elegance of the design of this invention, designing around it is very difficult, if not impossible. Nonetheless, many changes may be made to the design without deviating from the spirit of this invention. Examples of such contemplated variations include the following:
1. The shape and size of various members may be modified to accommodate a variety of body parts for users of different ages, genders, health, etc.
2. The color, aesthetics, materials, and thickness of the cast cover or the securing device may be varied.
3. Securing device elastic may be replaced by some other type of pleated fasteners.
4. Additional complimentary and complementary functions and features may be added.
5. Other accessories may be added such as a housing for holding a medical therapy or monitoring device.
6. The use of the device may include appendage protection during inclement weather.

Furthermore, other changes may be made such as aesthetics and substitution of newer materials as they become available. These changes, however, must perform substantially the same function in substantially the same manner with substantially the same result without deviating from the spirit of the invention. The following is a listing of components used in the best mode preferred embodiment and the alternate embodiments for use with OEM as well as retrofit markets. For the ready reference of the reader, the reference numerals have been arranged in ascending numerical order. It should be noted that in this legend of reference numbers, the first digit denotes the figure number and the remaining two digits connote the component reference number. 110 Embodiment of FIG. 1 generally 111 Stretch Vinyl Protective Sleeve 113 Molded V-ring 115 Opening Hole Closed End Intravenous (IV) Therapy Window Intravenous (IV) Therapy Hole FIG. 2 geometry Stretch Vinyl Protective Sleeve Molded V-ring Opening Hole Intravenous (IV) Therapy Window Intravenous (IV) Therapy Hole User's Hand FIG. 3 geometry Molded V-ring Opening Hole Intravenous (IV) Therapy Window Intravenous (IV) Therapy Hole FIG. 4 geometry Stretch Vinyl Protective Sleeve Molded V-ring Opening Hole Intravenous (IV) Therapy Window 420 Intravenous (IV) Therapy Hole 510 FIG. 5 geometry 511 Stretch Vinyl Protective Sleeve Molded V-ring Opening Hole Closed End Intravenous (IV) Therapy Window Intravenous (IV) Therapy Hole 610 FIG. 6 geometry Molded V-ring Stretch Vinyl Protective Cap.

Definitions and Acronyms

Great care has been taken to use words with their conventional dictionary definitions. The following definitions are included here for clarification. 3D=Three Dimensional DIY=Do It Yourself Interface=Junction between two dissimilar entities IV=Intravenous Therapy patch and line MTBF=Mean Time between Failures OEM=Original Equipment Manufacturer System=Synergistic cooperation of components.

While the invention has been described with reference to illustrative embodiments, this description is not intended to be construed in a limiting sense. Various modifications and combinations of the illustrative embodiments as well as other embodiments of the invention will be apparent to a person of average skill in the art

The invention claimed is:

1. A shower and water proofing protective sleeve for a cast and intravenous (IV) site comprising a tubular stretch vinyl sleeve wherein said stretch vinyl sleeve having two open ends; and wherein the ends include an integrally molded stretch vinyl band attached to each of said open ends, and where at least one of said ends include an integrally molded V-ring around said open end forming a water-tight seal around a limb.

2. A shower and water proofing protective sleeve for a cast and intravenous (IV) site of claim 1, wherein the sleeve has a tubular diameter which accommodates a limb or torso.

3. A shower and water proofing protective sleeve for a cast and intravenous (IV) site of claim 1, wherein said integrally molded v-ring has a smaller diameter than the diameter of the sleeve.

4. A shower and water proofing protective sleeve for a cast and intravenous (IV) site of claim 1, wherein one of said open ends of said sleeve is closed.

5. A shower and water proofing protective sleeve for a cast and intravenous (IV) site of claim 1, further including a pocket disposed within the sleeve to accommodate a medical therapy or monitoring device.

6. A shower and water proofing protective sleeve for a cast and intravenous (IV) site of claim 1, wherein the tubular sleeve further comprises an intravenous therapy window for protecting an IV site including an integrally molded hole for sealing and protecting the IV site.

\* \* \* \* \*